United States Patent
Okada et al.

(10) Patent No.: US 9,233,142 B2
(45) Date of Patent: Jan. 12, 2016

(54) THERAPEUTIC AGENT FOR INFECTIONS, AND TREATMENT METHOD USING SAME

(71) Applicants: NATIONAL HOSPITAL ORGANIZATION, KINKI-CHUO CHEST MEDICAL CENTER, partial interest, Osaka (JP); AZBIO CORPORATION, partial interest, Osaka (JP); Masaji Okada, partial interest, Osaka (JP); Yasushi Takamori, partial interest, Tokyo (JP)

(72) Inventors: Masaji Okada, Osaka (JP); Yasushi Takamori, Tokyo (JP); Kazuyuki Ogawa, Saitama (JP); Kinya Nagata, Saitama (JP)

(73) Assignees: National Hospital Organization Kinki-chuo Chest Medical center, Kita-ku, Sakai, Osaka (JP), partial interest; Masaji Okada, Higashi-ku, Sakai-shi, Osaka (JP), partial interest; AZBIO Corporation, Kita-ku, Osaka (JP), partial interest; Yasushi Takamori, Nerima-ku, Tokyo (JP), partial interest (*) Notice: Subject to any disclaimer, the term of this patent is extended or adjusted under 35 U.S.C. 154(b) by 0 days.

(21) Appl. No.: 14/292,940

(22) Filed: Jun. 2, 2014

(65) Prior Publication Data

US 2014/0308240 A1 Oct. 16, 2014

Related U.S. Application Data

(60) Division of application No. 13/604,645, filed on Sep. 6, 2012, now abandoned, which is a division of application No. 12/386,974, filed on Apr. 24, 2009, now Pat. No. 8,288,509, which is a continuation-in-part of application No. 10/921,091, filed on Aug. 17, 2004, now abandoned, which is a continuation of application No. PCT/JP03/01970, filed on Feb. 24, 2003.

(30) Foreign Application Priority Data

Feb. 22, 2002 (JP) .................................. 2002-45865

(51) Int. Cl.
 A61K 38/20 (2006.01)
 A61K 39/04 (2006.01)
 A61K 38/16 (2006.01)
 A61K 38/17 (2006.01)

(52) U.S. Cl.
 CPC ............. *A61K 38/20* (2013.01); *A61K 38/164* (2013.01); *A61K 38/1709* (2013.01); *A61K 38/1729* (2013.01); *A61K 38/204* (2013.01); *A61K 38/208* (2013.01); *A61K 39/04* (2013.01)

(58) Field of Classification Search
 None
 See application file for complete search history.

(56) References Cited

U.S. PATENT DOCUMENTS

| | | | |
|---|---|---|---|
| 5,700,776 A | 12/1997 | Ohneda et al. | |
| 6,485,928 B2 * | 11/2002 | Stenger et al. | 435/32 |
| 7,160,696 B2 | 1/2007 | Sordillo | |
| 7,459,439 B2 | 12/2008 | Modlin et al. | |
| 8,202,835 B2 * | 6/2012 | Hillman | 514/2.4 |
| 8,288,509 B2 * | 10/2012 | Okada et al. | 530/300 |
| 8,357,365 B2 * | 1/2013 | Kim | 424/94.64 |
| 8,426,366 B2 | 4/2013 | Hillman | |
| 8,815,229 B2 * | 8/2014 | Krensky et al. | 424/85.2 |
| 2002/0044927 A1 | 4/2002 | Stenger et al. | |
| 2005/0239699 A1 * | 10/2005 | Okada et al. | 514/12 |
| 2005/0249699 A1 | 11/2005 | Stoff et al. | |
| 2009/0274651 A1 * | 11/2009 | Okada et al. | 424/85.2 |
| 2012/0195854 A1 * | 8/2012 | Krensky et al. | 424/85.2 |
| 2013/0011366 A1 * | 1/2013 | Okada et al. | 424/85.2 |
| 2014/0308240 A1 * | 10/2014 | Okada et al. | 424/85.2 |
| 2015/0023910 A1 * | 1/2015 | Krensky et al. | 424/85.2 |

FOREIGN PATENT DOCUMENTS

WO WO 2008/090425 * 7/2008

OTHER PUBLICATIONS

Clayberger et al, The Journal of Immunology, 2012, 188: 6119-6126.*
Okada et al, Human Vaccines & Immunotherapeutics 9:3, 515-525; Mar. 2013.*
Kita et al, Human Vaccines & Immunotherapeutics 9:3, 526-533; Mar. 2013.*

(Continued)

*Primary Examiner* — Nita M Minnifield
(74) *Attorney, Agent, or Firm* — Curtis L. Harrington; Harrington & Harrington

(57) ABSTRACT

(Problems) To provide a therapeutic agent for infections comprising granulysin as an active ingredient which has little side effect and no cytotoxicity and to which bacteria can hardly acquire resistance, and a treatment method using the same.
(Means for Solving Problems) The present invention provides a therapeutic agent for infections comprising as active ingredient: 15K granulysin, a combination of 15K granulysin and 15K granulysin in vivo expression vector, a combination of 15K granulysin and at least one interleukin selected from IL-6, IL-23 or IL-27, a combination of 15K granulysin in vivo expression vector and at least one interleukin selected from IL-6, IL-23 or IL-27, or a combination of 15K granulysin in vivo expression vector and HSP65DNA and IL-12DNA in vivo expression vector, which enhances killing effects on bacteria and has less side effect, and to which bacteria can hardly acquire resistance, and a treatment method using the same.

1 Claim, 14 Drawing Sheets

(56) References Cited

OTHER PUBLICATIONS

Liu et al, Wuhan Daxue Xuebao (Yixue Ban), (May 2011) vol. 32, No. 3, pp. 292-295 abstract only.*
Miao et al, Zhonghua Shiyan He Linchuang Ganranbing Zazhi, Dianziban (2012), 6(5), 22-25 abstract only.*
Thuong et al, Respirology, (Nov. 2013) vol. 18, Supp. Suppl. 4, pp. 72. Abstract Number: OS223. Meeting Info: 18th Congress of the Asian Pacific Society of Respirology. Yokohama, Japan. Nov. 11-14, 2013.*
Yang et al, Mianyixue Zazhi (2009), 25(6), 685-688 abstract only.*
Waters et al, Clinical and Developmental Immunology vol. 2011, Article ID 768542, 11 pages.*
Kaufmann, Lancet Infect Dis 2011;11: 633-40.*
Yang et al 2008, Chinese Journal of Biologicals, (Jul. 2008) vol. 21, No. 7, pp. 545-548 abstract only.*
Clayberger et al The Journal of Immunology, 2012, 188: 6119-6126.*
Finn et al, Protein Expression and Purification 75 (2011) 70-74.*
Guo et al, Appl Microbiol Biotechnol (2013) 97:7669-7677.*
Lu et al, J. Leukoc. Biol. 2014, vol. 96. 11 pages, Epub ahead of print Aug. 19, 2014—doi:10.1189/jlb.4A0713-363RR.*
D. Veljkovic Vujaklija et al., Journal of Reproductive Immunology 97 (2013) 186-196.*
Stenger, S. et al, "An Antimicrobial Activity of Cytolytic T Cells Mediated by Granulysin" Science 282, 121-125 (1998).
Pena, S.V et al., "Processing, Subcellular Localization, and Function of 519 (Granulysin), a Human Late T Cell Activation Molecule with Homology to Small, Lytic, Granule Proteins" J.Immunol, 158, 2680-2688 (1997).
Canaday, David H. et al., "CD4+ and CD8+ T Cells Kill Intracellulat Mycobacterium tuberculosis by a Perforin and Fas/Fas Ligand-Independent Mechanism" J. Immunol, 167,2734-2742 (2001).
Jongstra, et al.,"The Isolation and Sequence of a Novel Gene from a Human Functional T Cell Line" J. exp. Med,165,601-614 (1987).
Yabe, Toshio et al, "A cDNA Clone Expressed in Natural Killer and T Cells that Likely Encodes a Secreted Protein" J.Exp.Med., 172:1159-1163 (1990).
WIPO publication No. W099/22755 Al, Stenger, Steffen, et al. "Use of Granulysin as an Antimicrobial Agent".
MA Ling LAng et al, Anticryptocoocal activity of mitogen stimulated primary human CD8+ T cells mediated by granulysin. FASEB Journal, 2001, vol. 15, No. 5, pp. A1009, 774.20, 1.8-10, 15-16.
Krensky et al. "A Novel Antimicrobial Peptide of Cytolytic T Lymphocytes and Natural Killer Cells" Biochemical Pharmacology vol. 159, pp. 317-320 2000.
Clayberger et al. "Granulysin" Current Opinion in Immunology 2003, p. 560-565.
Kumar et al. "Expert Opinion on Investigational Drugs: Granulysin: a novel antimicrobial" Oct. 2, 2001: p. 321-329.
Mackewicz, Carl E, "HIV virions and HIV replication are unaffected by granulysin" AIDS vol. 14, p. 328-330.
Yu et al., "Delivery Delivery and Delivery" Gene Therapy (2006)p. 1-2.
Tjuvajev JG et al. "Imaging Adrenoviral-mediated Herpes Virus Thymidine Kinase Gene Transfer and Expression In Vivo" Cancer Res. Oct. 15, 1999 V59 p. 5186-5193.
Bramson et al. Pre-esisting Immunity to Adenovirus does not prevent tumor regression following intraumoral administration of a vector expressing IL-12 but Inhibits Virus Dissemination. Gene Therapy V4 (1997) p. 1069-E076.
Thomas CE et al. "Imaging Adenoviral-mediated Herpes Virus Thymidine Kinase Gene Transfer and Expression In Vivo" Nature Reviews Genetics V4, May 2003 p. 347-358.
Boissier et al. "Therapeutic Gene Transfer for Rheumatoid Arthritis" Renmatismo 2004; 56-N. 1 (Suppl. 1) p. 51-61.

Bambridge J. W. B et al "Gene Therapy for Ocular Angiogenesis" Clinical Science (2003) p. 561-575.
Verma IM, "Gene Therapy—Promises, Problems and Prospects" Somia N. Nature vol. 389 Sep. 1997, 239-242.
Vanin EF et al. "Characterization of Replication—Competent Retroviruses from Nonhuman Primates with Virus-Induced T-Cell Lymphomas and Observations Regarding the Mechanism of Oncogenesis" Journal of Virology Jul. 1994,p. 4241-4250.
Chong H et al. "A Replication-Competent Retrovirus Arising from a Split-Function Packaging Cell Line Was Generated by Recombination Events between the Vector, One of the Packaging Constructs, and Endogenous Retroviral Sequences" Journal of Virology Apr. 1998 p. 2663-2670.
Dennis A Hanson et al, "Biosynthesis of Granulysin, A Novel Cytolytic Molecule" Molecular immunology 36 (1999), 413-421.
Kaufmann, H.E., "Cell-mediated immunity: Dealing a Direct Blow to Pathogens"8., 1999 Current Biology vol. 9, No. 3, p. 97-R99.
European Patent Application No. EP0320806 A "T-cell activation related gene" published Jun. 21, 1989.
Japan Patent Publication No. JP7-69921 (with English abstract), published on Mar. 14, 1995; title only in Japanese.
WIPO publication No. WO02/21651, entitled "Laser System with External Optical Feedback and Use of Such System in the Graphical Industry" of Inventor: Petersen, Paul Michael.
Okada et al,"The development of novel vaccines against Tuberculosis" Jpn.J.Clin.Immunol.,31 (5) 356-368 (2008).
Wallis et al "Cytokynes & Tuberculosis" J. Leukoc. Biol, 1994, 55:676681 (Ex added 2-16-2-2011).
R&D Systems Catalog. Recombinant Human Granulysin Apr. 30, 2009, Catalog #: 3138-GN/CF (Ex added 2-16-2-2011).
Khader et al, Nature Immunology, Apr. 2007, 8/4: 369-377 (Ex added 2-16-2-2011).
Pena, Susan V. and Alan M. Krensky "Granulysin, a new human cytolytic granule-associated protein with possible involvement in cell-mediated cytotoxicity" Pena et al, Seminars in Immunology, 1997, 9:117-125 (Ex added 2-16-2-2011).
Andersson et al, Infection and immunity, Nov. 2007, 75/11:5210-5222(Ex. added May 26, 2010).
Ernst et al, "Granulysin a T-Cell Product, Kills Bacteria by Altering Membrane Permeability" J. Immunology, 2000, 165:7101-7108(Ex. added May 26, 2010).
Krensky et al, "Biology and Clinical Relevance of Granulysin" Tissue Antigens, Mar. 2009, 73/3: 193-198 (Ex. added May 26, 2010).
European Search Report of Nov. 10, 2010 of 09171752.0-2107 / 2243489 citing six references.
EP 1 484 066 A1 (Nat Kini chou hospital for children [jp]; Okada Masaji [JP] Nat Hospital OR, Dec. 8, 2004 (ESP of Nov. 10, 2010).
Yang Chun et al: Comparative study on roles of Mycobacterium smegmatis and BCG as vectors in treatment of tuberculosis in mouse model Chinese Journal of Biologicals vol. 21, No. 7, Jul. 2008, pp. 545-548, XP001539719 ISSN: 1004-5503 * abstract; table I * (ESP of Nov. 10, 2010).
Okada N el al.: "Novel Therapeutic Vaccination (granulysin DNA, adenovlrial vectro/rL-6 related genes) against Tuberculosis"FASEB J., vol. 22, LB491, 2008, XP009136050 * abstract *(ESP of Nov. 10, 2010).
Krensky A M et al: "Biology and clinical relevance of granulysin" TISSUE ANTIGENS, vol. 73, No. 3, Mar. 2009,pp. 193-198, XP009136038, ISSN: 0001-2815. Abstract* p. 193, col. I *; * p. 395, col. 1-col. 2 * (ESP of Nov. 10, 2010).
Kita et al, Human Vaccines 7: Supplement, 108-114; Jan./Feb. 2011 is entitled "Development of Therapeutic and Prophylactic Vaccine Against Tuberculosis Using Monkey and Transgenic Mice Models".
Okada et al, hUMAN vACCINES 6:4, 297-308; Apr. 2010 is entitled "Tuberculosis Vaccine Development—The Development of Novel (Preclinical) DNA Vaccine".

* cited by examiner

Liver

\*   P<0.05
\*\*  15K Protein: 15K granulysin recombinant protein
\*\*\* 15K Vector: 15K granulysin in vivo expression vector

* $P < 0.05$
** 15K Protein: 15K granulysin recombinant protein
*** IL-6: Interleukin-6

Spleen

*     P<0.05
**   15K Vector: 15K granulysin in vivo expression vector
***   IL-6: Interleukin-6

Liver

*    P<0.05
**  15K Protein: 15K granulysin recombinant protein
***  IL-6: Interleukin-6

Lung

*     $P < 0.05$
**    15K Protein: 15K granulysin recombinant protein
***   IL-6: Interleukin-6

Liver

\*    P<0.05

\*\*   15K Protein: 15K granulysin recombinant protein

\*\*\*  15K Vector: 15K granulysin in vivo expression vector

Spleen

\* P<0.05
\*\* 15K Protein: 15K granulysin recombinant protein
\*\*\* 15K Vector: 15K granulysin in vivo expression vector Spleen \*     $P < 0.05$
\*\*    15K Protein: 15K granulysin recombinant protein
\*\*\*   IL-23: Interleukin-23

Liver

*   P<0.05
**  15K Protein: 15K granulysin recombinant protein
*** IL-23: Interleukin-23

Lung

\*     P<0.05
\*\*   15K Protein: 15K granulysin recombinant protein
\*\*\*   IL-23: Interleukin-23

Spleen

\* P＜0.05
\*\* 15K Vector: 15K granulysin in vivo expression vector
\*\*\* IL-23: Interleukin-23

Lung

*    P＜0.05
**  15K vector: 15K granulysin in vivo expression vector
***   IL-27: Interleukin-27

Liver

\*     $P < 0.05$
\*\*    15K vector: 15K granulysin in vivo expression vector
\*\*\*   HSP65&IL-12 Vectors: HSP65DNA and IL-12 DNA in vivo expression vectors

SEQUENCE LISTING

<160> NUMBER OF SEQ ID NOS: 4

<210> SEQ ID NO 1
<211> LENGTH: 745
<212> TYPE: DNA
<213> ORGANISM: Homo sapiens
<220> FEATURE:
<221> NAME/KEY: CDS
<222> LOCATION: (129)..(563)

<400> SEQUENCE: 1
gtatctgtgg taaacccagt gacacggggg agatgacata caaaaagggc aggacctgag     60
aaagattaag ctgcaggctc cctgcccata aaacagggtg tgaaaggcat ctcagcggct    120 gccccacc atg gct acc tgg gcc ctc ctg ctc ctt gca gcc atg ctc ctg    170
         Met Ala Thr Trp Ala Leu Leu Leu Leu Ala Ala Met Leu Leu -continued

```
                 1               5                    10
ggc aac cca ggt ctg gtc ttc tct cgt ctg agc cct gag tac tac gac      218
Gly Asn Pro Gly Leu Val Phe Ser Arg Leu Ser Pro Glu Tyr Tyr Asp
 15              20                   25                   30 ctg gca aga gcc cac ctg cgt gat gag gag aaa tcc tgc ccg tgc ctg      266
Leu Ala Arg Ala His Leu Arg Asp Glu Glu Lys Ser Cys Pro Cys Leu
                 35                   40                   45 gcc cag gag ggc ccc cag ggt gac ctg ttg acc aaa aca cag gag ctg      314
Ala Gln Glu Gly Pro Gln Gly Asp Leu Leu Thr Lys Thr Gln Glu Leu
             50                   55                   60 ggc cgt gac tac agg acc tgt ctg acg ata gtc caa aaa ctg aag aag      362
Gly Arg Asp Tyr Arg Thr Cys Leu Thr Ile Val Gln Lys Leu Lys Lys
             65                   70                   75 atg gtg gat aag ccc acc cag aga agt gtt tcc aat gct gcg acc cgg      410
Met Val Asp Lys Pro Thr Gln Arg Ser Val Ser Asn Ala Ala Thr Arg
 80                   85                   90 gtg tgt agg acg ggg agg tca cga tgg cgc gac gtc tgc aga aat ttc      458
Val Cys Arg Thr Gly Arg Ser Arg Trp Arg Asp Val Cys Arg Asn Phe
 95                  100                  105                  110 atg agg agg tat cag tct aga gtt acc cag ggc ctc gtg gcc gga gaa      506
Met Arg Arg Tyr Gln Ser Arg Val Thr Gln Gly Leu Val Ala Gly Glu
                115                  120                  125 act gcc cag cag atc tgt gag gac ctc agg ttg tgt ata cct tct aca      554
Thr Ala Gln Gln Ile Cys Glu Asp Leu Arg Leu Cys Ile Pro Ser Thr
             130                  135                  140 ggt ccc ctc tgagccctct caccttgtcc tgtggaagaa gcacaggctc              603
Gly Pro Leu
        145 ctgtcctcag atcccgggaa cctcagcaac ctctgccggc tcctcgcttc ctcgatccag    663 aatccactct ccagtctccc tccctgact ccctctgctg tcctcccctc tcacgagaat     723 aaagtgtcaa gcaagaaaaa aa                                             745

<210> SEQ ID NO 2
<211> LENGTH: 24
<212> TYPE: DNA
<213> ORGANISM: Homo sapiens

<400> SEQUENCE: 2
catctcagcg gctgccccac catg                                           24

<210> SEQ ID NO 3
<211> LENGTH: 27
<212> TYPE: DNA
<213> ORGANISM: Homo sapiens

<400> SEQUENCE: 3 tgtataccttt ctacaggtcc cctctga                                       27

<210> SEQ ID NO 4
<211> LENGTH: 29
<212> TYPE: PRT
<213> ORGANISM: Homo sapiens

<400> SEQUENCE: 4

Arg Thr Gly Arg Ser Arg Trp Arg Asp Val Cys Arg Asn Phe Met Arg
 1               5                   10                  15

Arg Tyr Gln Ser Arg Val Thr Gln Gly Leu Val Ala Gly
             20                  25
```

THERAPEUTIC AGENT FOR INFECTIONS, AND TREATMENT METHOD USING SAME

CROSS REFERENCE TO RELATED APPLICATION

This application is a divisional application of co-pending U.S. patent application Ser. No. 13/604,645 filed on Sep. 6, 2012 which was a divisional application of co-pending U.S. patent application Ser. No. 12/386,974 filed on Apr. 24, 2009 which was a continuation-in-part of then co-pending U.S. patent application Ser. No. 10/921,091 filed Aug. 17, 2004. U.S. patent application Ser. No. 10/921,091 is based on and claims priority to Japanese Patent Application No. 2002-45865, (Filed on Feb. 22, 2002,—(based upon and through PCT/JP2003/001970) and the entire content of which is incorporated herein by reference.

FIELD OF THE INVENTION

The present invention relates to a therapeutic agent for treating infectious diseases such as *tuberculosis*, and a treatment method using the same.

BACKGROUND OF THE INVENTION

In medical care, it goes without saying that a therapeutic agent for infectious diseases is indispensable. At present, a number of therapeutic agents for infections such as antibiotics and synthetic antibacterial agents are provided to be used in medical care.

However, currently, an antibacterial agent which is mainly provided as therapeutic agent for infections has in fact an unavoidable problem; appearance of drug resistant bacteria. That is, a new antibacterial agent leads to produce a new drug resistant bacterium, and such a sarcastic state continues until now.

For example, *tuberculosis* occupies the first position of a death rate among single infectious diseases, and its increasing tendency becomes a worldwide problem. Further, a drug resistant bacterium having resistance to almost all antibiotics has been confirmed, and this problem has been obvious.

Recently, it has been revealed that granulysin, which is a molecule expressed in Natural Killer cells (NK cell) or Cytotoxic T Lymphocytes (CTL), has direct ability to kill and injure bacteria such as *Mycobacterium tuberculosis* [Stenger, S. et al., Science 282, 121-125 (1998)].

Granulysin is produced as a precursor of 15K and, thereafter, processed into 9K in a cytotoxic granule. It is known that this 9K granulysin has antibacterial activity (Pena, S. V. et al., J. Immunol, 158, 2680-2688 (1997)).

However, it is necessary to use a perform, which is a molecule derived from the same cytotoxic intragranule, to allow 9K granulysin to show the antibacterial activity. This is because perform perforates a target cell, 9K granulysin enters into the cell therethrough, and 9K granulysin introduced into the target cell kills and injures an infecting bacterium in the cell [Stenger, S. et al., Science 282, 121-125 (1998)].

Accordingly, it is necessary to administer perform simultaneously to use 9K granulysin as a therapeutic agent for infections. However, as described above, perform shows cytotoxicity (Pena, S. V. et al., J. Immunol, 158, 2680-2688 (1997)), and therefore its administration may cause considerable side effects.

In addition, the present inventors produced 9K granulysin transgenic mouse and 15K granulysin transgenic mouse, then intravenously administered $5 \times 10^5$ CFU of H37Rv *Mycobacterium tuberculosis* through tail vein in each mouse and a wild-type control mouse respectively, and after 4 weeks, measured the numbers of *Mycobacterium tuberculosis* in lungs of each mouse, and confirmed that the number of *Mycobacterium tuberculosis* in the lung of 15K granulysin transgenic mouse is more reduced than that of 9K granulysin transgenic mouse with a statistically significant difference ($p<0.05$; Student's t Test). Thus, the present inventors are the first to find that 15K granulysin has significantly stronger killing effect and suppressing effect on *Mycobacterium tuberculosis* in vivo than 9K granulysin. In addition, the result suggests that 9K Granulysin has very weak suppressing effect on *Mycobacterium tuberculosis* in vivo.

SUMMARY OF INVENTION

Based on the above aspects, the present invention provides a therapeutic agent for infections, to which bacteria acquire less resistance, and which has different characteristics from antibiotics, and has no cytotoxicity and less side effects. Also, the present invention provides a treatment method using the therapeutic agent.

In order to solve these problems, the present inventors intensively studied. As a result, the present inventors found out a novel pathway, wherein 15K granulysin remains as itself without receiving its processing outside cells, while it is introduced into a macrophage without being perforated by perform, thereafter, it becomes activated to kill and injure bacteria phagocytosed into a macrophage.

That is, the present inventors found out that use of 15K granulysin showing no cytotoxicity itself as an active ingredient makes it possible to provide an efficacious therapeutic agent for infections which has little side effect and to which bacteria can hardly acquire resistance, and a treatment method using the therapeutic agent.

Further, the present inventors found out that, in addition to administrating 15K granulysin, an administration of a vector in which a gene encoding 15 K granulysin is incorporated to express 15K granulysin in vivo (hereinafter referred to as "15K granulysin in vivo expression vector") shows no cytotoxicity and stronger killing effect on bacteria than that of 15K granulysin itself or of 15K granulysin in vivo expression vector itself.

Further, the present inventors found out that, in addition to administrating 15K granulysin, an administration of at least one interleukin selected from the group consisting of interleukin 6 (hereinafter referred to as "IL-6"), interleukin 23 (hereinafter referred to as "IL-23") and interleukin 27 (hereinafter referred to as "IL-27") shows no cytotoxicity and stronger killing effect on bacteria than that of 15K granulysin itself or at least one interleukin selected from the group consisting of interleukin 6, interleukin 23 and interleukin 27 itself.

Furthermore, the present inventors found out that, in addition to administrating 15K granulysin in vivo expression vector, an administration of at least one interleukin selected from the group consisting of IL-6, IL-23 and IL-27 shows stronger killing effects on bacteria than that of 15K granulysin in vivo expression vector itself or at least one interleukin selected from the group consisting of interleukin 6, interleukin 23 and interleukin 27 itself.

Next, in addition to administrating the 15K granulysin in vivo expression vector, HVJ-envelope HSP65DNA and IL-12 DNA in vivo expression vectors on *Mycobacterium tuberculosis* (*M. tuberculosis*) created by the present inventors (Okada et al, Jpn. J. Clin. Immunol., 31 (5) 356-368 (2008)) (Hereinafter, referred to as "HSP65DNA and IL-12DNA in vivo expression vectors") were administered. This HSP65 DNA and IL-12DNA in vivo expression vectors show the strongest treatment effect to not only mouse family but also *Macaca fascicularis* family which is considered as the closest model to human in terms of *tuberculosis* infection.

HSP65DNA and IL-12DNA in vivo expression vectors are prepared by incorporating 65 KDa heat-shock protein DNA (HSP65DNA) of *M. tuberculosis* H37Rv and IL-12 DNA into an envelope of Sendai virus (HVJ), and it is known to show a strong treatment effect on *M. tuberculosis*. It was confirmed that an administration of 15K granulysin in vivo expression vector in addition to the HSP65DNA and IL-12DNA in vivo expression vectors further improved killing effect on *M. tuberculosis*.

The present invention provides a therapeutic agent for infections comprising 15K granulysin as an active ingredient, which is effective and has no side effect, and a treatment method using the same. Also, the present invention provides a therapeutic agent comprising a combination of 15K granulysin and 15K granulysin in vivo expression vector, a combination of 15K granulysin and at least one interleukin selected from IL-6, IL-23 or IL-27, a combination of 15K granulysin in vivo expression vector and at least one interleukin selected from IL-6, IL-23 or IL-27, or a combination of 15K granulysin in vivo expression vector and HSP65DNA and IL-12DNA in vivo expression vectors, which has no side effect and shows killing effect on *M. tuberculosis*, and a treatment method using the same.

DETAILED DESCRIPTION OF THE INVENTION

Figure 1:
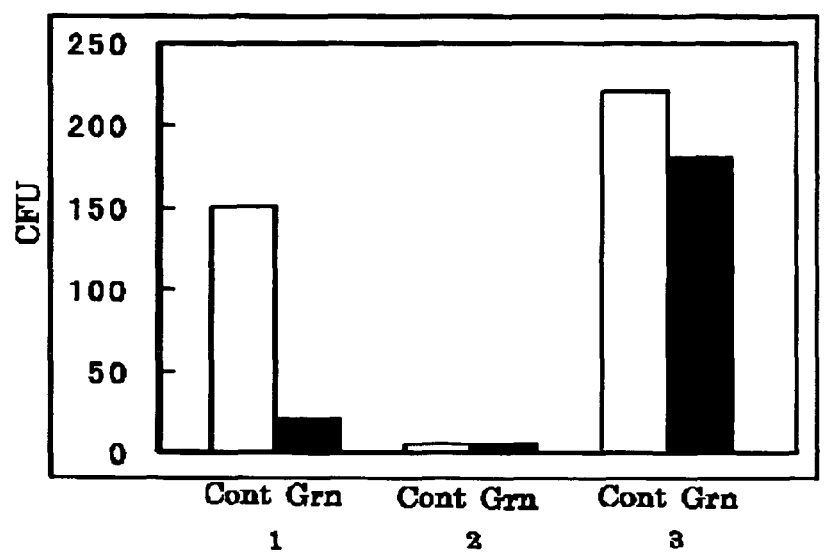
FIG. 1 is a view showing antibacterial effects of 15K granulysin on *M. tuberculosis*.

Embodiments of the present invention will be explained below.
A. Active Ingredient of Present Therapeutic Agent 15K granulysin used as an active ingredient of the present therapeutic agent may be obtained by being separated from a living body. However, since 15K granulysin is a trace component in a living body, it is preferable to be used as a recombinant protein obtained by expressing a gene encoding 15K granulysin. Alternatively, it is also a suitable means to produce 15K granulysin in a living body, utilizing 15K granulysin in vivo expression vector in which a gene encoding 15K granulysin is incorporated, as an active ingredient.
B. Preparation of 15K Granulysin Recombinant Protein A sequence of a gene encoding 15K granulysin has been already reported (Jongstra, et al., J. Exp. Med, 165, 601), specifically, a gene having a nucleotide sequence represented by SEQ ID NO: 1. Based on this, a gene encoding 15K granulysin is effectively prepared to express this gene, which results in preparing a recombinant protein of 15K granulysin.

Specifically, the nucleotide chains that are complementary to both ends of a sequence of a gene encoding 15K granulysin are used as amplification primers, and a gene amplification method such as a PCR method is used to prepare a gene amplification product of the gene encoding 15K granulysin.

This is incorporated into a suitable gene expression vector, and suitable host such as *Escherichia coli, Bacillus subtilis*, yeast and insect cell is transformed with such the recombinant vector so as to produce a desired 15K granulysin.

It is preferable that, as a gene expression vector used herein, a vector having a promoter and an enhancer at a region upstream of a gene to be expressed, and a transcription termination sequence at a region downstream of the gene is used.

In addition, an expression of a 15K granulysin gene is not limited to a direct expression system. For example, a fused protein expression system utilizing a β-galactosidase gene, a glutathione-S-transferase gene or a thioredoxin gene may be used.

As a gene expression vector using *Escherichia coli* as a host, there are exemplified pQE, pGEX, pT7-7, pMAL, pTrx-Fus, pET, and pNT26CII. As a gene expression vector using *Bacillus subtilis* as a host, there are exemplified pPL608, pNC3, pSM23, and pKH80.

In addition, as a gene expression vector using yeast as a host, there are exemplified pGT5, pDB248X, pART1, pREP1, YEp13, YRp7, and YCp50.

In addition, as a gene expression vector using a mammal cell or an insect cell as a host, there are exemplified p91023, pCDM8, pcDL-SRα296, pBCMGSNeo, pSV2dhfr, pSVdhfr, pAc373, pAcYM1, pRc/CMV, pREP4, and pcDNAI.

These gene expression vectors may be selected depending on the purpose of expression of 15K granulysin. For example, when 15K granulysin is expressed, it is preferable to select a gene expression vector for which *Escherichia coli, Bacillus*

*subtilis* or yeast may be selected as a host. When 15K granulysin is expressed to show an assuredly activity even at a small amount, it is preferable to select a gene expression vector for which a mammal cell or an insect cell may be selected as a host.

In addition, it is possible to select the existing gene expression vector as described above, but a gene expression vector may be appropriately produced depending on a purpose, and this may be of course used.

Transfection of the above-mentioned gene expression vector in which a 15K granulysin gene is incorporated, into a host cell, and a transformation method therewith may be performed by the general method, for example, a calcium chloride method, and an electroporation method are used in the case of using *Escherichia coli* and *Bacillus subtilis* as a host cell, and a calcium phosphate method, an electroporation method and a liposome method are used in the case of using a mammal cell and an insect cell as a host.

The obtained transformant is cultured according to the conventional methods so as to accumulate a desired 15K granulysin. Medium used in such the culture may be appropriately selected depending on the characteristics of a host. For example, LB medium and TB medium may be appropriately used in the case of using *Escherichia coli* as a host, and RPMI1640 medium may be appropriately used in the case of using mammal cells as a host.

15K granulysin may be isolated and purified from the obtained culture according to the conventional method. For example, various treating operations utilizing physical and/or chemical nature of 15K granulysin may be used.

Specifically, treatment with a protein precipitating agent, ultrafiltration, gel filtration, high performance liquid chromatography, centrifugation, electrophoresis, affinity chromatography using a specific antibody, and dialysis method can be used alone or by combining these methods.

As described above, 15K granulysin can be separated and purified. By using 15K granulysin as an active ingredient in a therapeutic agent for infections, it is introduced into a macrophage in blood, and activated therein to kill and injure infection-inducing bacteria, viruses and fungi which have been phagocytosed by a macrophage. This enables to treat infectious diseases caused by these microoraganisms. As described above, unlike 9K granulysin, 15K granulysin does not show cytotoxicity in per se, and its effects as a therapeutic agent for infectious diseases having little side effect due to administration are expected.

C. Preparation of 15K Granulysin In Vivo Expression Vector

An active ingredient of the present therapeutic agent is a recombinant vector, which is an in vivo expression vector in which a gene encoding 15K granulysin used for expressing the aforementioned recombinant protein is incorporated.

Examples of the in vivo expression vector are not limited to, but include an adenovirus vector and a retrovirus vector. For an in vivo expression vector, for example, the aforementioned virus gene is incorporated into a cosmid vector, and a gene capable of expressing 15K granulysin is further incorporated into the cosmid vector and then, this cosmid vector and a parent virus DNA-TP which has been treated with a restriction enzyme are transfected into 293 cells, whereby, homologous recombination occurs in the 293 cells, thus, a desired in vivo expression vector is produced.

D. Present Therapeutic Agent Comprising 15K Granulysin Recombinant Protein as Active Ingredient, and Treating Method Using the Same According to one embodiment, the present therapeutic agent comprises 15K granulysin as an active ingredient and, at the same time, an appropriate pharmaceutical preparation carrier may be comprised to form a preparation composition (of course, only 15K glanulysin is possible). As a pharmaceutical preparation carrier, for example, excipients and diluents such as fillers, bulking agents, binders, wetting agents, stabilizers, solubilizers, disintegrating agents and surface active agents which are conventionally used as a pharmaceutical preparation carrier may be freely selected depending on a specific dosage form. A form of a preparation composition is not particularly limited as far as 15K granulysin is effectively used in treatments of infectious diseases. For example, solid agents such as tablets, powders, granules and pills, and also injectable forms such as solutions, suspensions and emulsions may be used. An appropriate carrier to 15K granulysin may be added to produce a dried agent, which is formulated to be liquid upon use.

A dose amount of the thus obtained present therapeutic agent may be appropriately selected depending on an administration method and an administration form of an agent, and symptom of a patient. It is preferable to administer 10,000 µg/50 kg of 15K granulysin protein, which is an active ingredient, once per day or by dividing into a few times per day, and 6 times at a few dates interval, but it is not limited thereto.

Such the various forms of pharmaceutical preparations may be administered by an appropriate administration route depending on its form, for example, by intravenous, intramuscular, intraosseous, intra-articular, subcutaneous, intracutaneous, or intraperitoneal administration in the case of an injectable form, or by oral or enteral administration in the case of a solid agent form.

E. Present Therapeutic Agent Comprising 15K Granulysin In Vivo Expression Vector as Active Ingredient and Treating Method Using the Same According to another embodiment, 15K granulysin in vivo expression vector is used as a therapeutic agent because 15K granulysin does not require perforin and it has an antibacterial effect. That is, perforin is required in the case of 9K granulysin, thus, even if a 9K granulysin in vivo expression vector is created, perforin should be administered to the area in which 9K granulysis is expressed, and therefore this is impractical. In addition, perforin may induce side effect if administered. However, 15K granulysin does not require perforin and 15K granulysin has antibacterial effect by itself, so that a 15K granulysin in vivo expression vector is used as an active ingredient in the therapeutic agent.

The in vivo expression vector, which is prepared as described above, is isolated and purified, and subsequently administrated to a living body in order to produce 15K granulysin in the living body, which results in exhibiting the pharmacological effect of 15K granulysin.

A dosage form of the 15K granulysin in vivo expression vector is generally an injectable form, and it may be administered by intravenous, intramuscular, intraosseous, intra-articular, subcutaneous, intracutaneous or intraperitoneal administration. A dose of the present therapeutic agent may be appropriately selected depending on an administration method and an administration form of an agent, and symptom of a patient, but being not limited.

Generally, it is preferable to appropriately administer 2,000 µg/50 kg of the 15K granulysin in vivo expression vector as an active ingredient once per day, and 6 times at a few dates interval.

F. Present Therapeutic Agent Comprising 15K granulsin Recombinant Protein and 15K Granulysin In Vivo Expression Vector as Active Ingredient and Treatment Method Using the Same)

Combined use of 15K granulsin recombinant protein and 15K granulysin in vivo expression vector enables to show stronger killing effect on bacteria than independent use of the above.

A form of the agent and an administration method are as described above. A dose amount may be appropriately selected depending on an administration method and an administration form of an agent, and symptom of a patient. It is preferable to administer 10,000 μg/50 kg of the 15K granulysin recombinant protein once per day or by dividing into a few times per day and 6 times at a few dates interval, while it is preferable to administer 2,000 μg/50 kg of the 15K granulysin in vivo expression vector once per day and 6 times at a few dates interval, but it is not limited thereto.

A dosage form of the 15K granulysin in vivo expression vector is generally an injectable form. Also, 15K granulysin in vivo expression vector may be prepared in an injectable form by adding an appropriate carrier thereto. Then, the 15K granulysin recombinant protein and the 15K granulysin in vivo expression vector in the injectable forms may be administered by intravenous, intramuscular, intraosseous, intra-articular, subcutaneous, intracutaneous, or intraperitoneal administration at the same time or alternately at a given interval.

G. Present Therapeutic Agent Comprising 15K Granulsin Recombinant Protein and at least one Interleukin Selected from Interleukin 6, Interleukin 23 or Interleukin 27 as Active Ingredient, and Treatment Method using the same Combined use of the 15K granulysin recombinant protein and at least one interleukin selected from interleukin 6, interleukin 23 or interleukin 27 as active ingredients enables to show killing effects on bacteria than independent use of the above materials.

According to yet another embodiment, the therapeutic agent comprises the 15K granulysin recombinant protein and at least one interleukin selected from interleukin 6, interleukin 23 or interleukin 27 as active ingredients. An appropriate pharmaceutical preparation carrier may be comprised thereto in order to form a preparation composition, as well as the case of using 15K granulysin recombinant protein by itself. As for a pharmaceutical preparation carrier, for example, excipients and diluents such as fillers, bulking agents, binders, wetting agents, stabilizers, solubilizers, disintegrating agents and surface active agents which are conventionally used as a pharmaceutical preparation carrier may be freely selected depending on a specific dosage form. A form of a preparation composition is not particularly limited as far as both the 15K granulysin recombinant protein and the at least one interleukin selected from interleukin 6, interleukin 23 or interleukin 27 are effectively used in treatments of infectious diseases. For example, solid agents such as tablets, powders, granules and pills, and also injectable forms such as solutions, suspensions and emulsions may be used. An appropriate carrier to the 15K granulysin recombinant protein and the at least one interleukin selected from interleukin 6, interleukin 23 or interleukin may be added to produce a dried agent, which is formulated to be liquid upon use.

A dose amount of such the therapeutic agent may be appropriately selected depending on an administration method and an administration form of an agent, and symptom of a patient. It is preferable to administer 10,000 μg/50 kg of 15K granulysin recombinant protein and 2,500 μg/50 kg in the case of IL6, 5,000 μg/50 kg in the case of IL23, or 2,500 μg/50 kg in the case of IL27, which are active ingredients, once per day or by dividing into a few times per day, and 6 times at a few dates to more than 1 week interval, but not limited thereto. The administrations of the two materials may be performed at the same time or alternately at a given interval.

Because a combination of 15K granulysin protein and interleukin exhibits strong killing effects on bacteria, it is possible to reduce the treatment times to 3 times.

Such the various forms of pharmaceutical preparations may be administered by an appropriate administration route depending on its form, for example, by intravenous, intramuscular, intraosseous, intra-articular, subcutaneous, intracutaneous, or intraperitoneal administration in the case of an injectable form, or by oral or enteral administration in the case of a solid agent form.

H. Present Therapeutic Agent Comprising 15K Granulsin In Vivo Expression Vector and at least one Interleukin Selected from Interleukin 6, Interleukin 23 or Interleukin 27 as Active ingredient and Treatment Method Using the Same Combined use of the 15K granulysin in vivo expression vector and the at least one interleukin selected from interleukin 6, interleukin 23 or interleukin 27 as active ingredients enables to show killing effects on bacteria than independent use of the above materials.

According to yet another embodiment, the present therapeutic agent comprises the 15K granulysin in vivo expression vector and the at least one interleukin selected from interleukin 6, interleukin 23 or interleukin 27 as active ingredients, and an appropriate pharmaceutical preparation carrier is also comprised thereto in order to form a preparation composition. A dose amount of such the therapeutic agent may be appropriately decided depending on an administration method and an administration form of an agent, and symptom of a patient. It is preferable to administer 2,000 μg/50 kg of the 15K granulysin in vivo expression vector once per day and 6 times at a few dates to more than 1 week interval, while it is preferable to administer 2, 500 μg/50 kg in the case of IL-6, 5, 000 μg/50 kg in the case of IL-23, and 2, 500 μg/50 kg in the case of IL-27, once per day or by dividing into a few times per day and 6 times at a few dates to more than 1 week interval, but it is not limited thereto.

A dosage form of the 15K granulysin in vivo expression vector is generally an injectable form. Also, the at least one interleukin selected from IL-6, IL-23, or IL-27 may be prepared in an injectable form by adding an appropriate carrier thereto. Then, the both materials in the injectable forms may be administered at the same time or alternately at a given interval.

I. Present Therapeutic Agent Comprising 15K Granulsin In Vivo Expression Vector and HSP65DNA and IL-12DNA in vivo expression vectors as Active Ingredient, and Treatment Method Using the Same A dosage form of the 15K granulsin in vivo expression vector and an HSP65DNA and IL-12DNA in vivo, expression vectors is generally an injectable form, and it may be administered by intravenous, intramuscular, intraosseous, intra-articular, subcutaneous, intracutaneous or intraperitoneal administration. A dose of such the present therapeutic agent may be appropriately selected depending on an administration method and an administration form of an agent, and symptom of a patient, but being not limited.

Generally, it is preferable to administer 2,000 μg/50 kg of 15K granulysin in vivo expression vector and 2,000 μg/50 kg of the HSP65DNA and IL-12DNA in vivo expression vectors, which are active ingredients, once per day, and 6 times at a few dates interval.

Because a combination of 15K granulysin in vivo expression vector and HSP65DNA and IL-12DNA in vivo expression vectors exhibits strong killing effects on bacteria, it is possible to reduce the treatment times to 3 times.

EXAMPLE

Examples of the present invention will be described below.

Test Example

Study of Antibacterial Effect on *Mycobacterium tuberculosis* (*M. tuberculosis*) when 15K Granulysin and a Macrophage are Present Together (1) Preparation of Monoclonal Antibody Specific for 15K Granulysin A RNA was extracted from human peripheral blood lymphocyte which had been cultured in the presence of 100 to 200 unit/ml of IL-2 ($2 \times 10^6$ cells/ml of human peripheral blood lymphocytes were cultured at 37° C. under 5% $CO_2$ incubator for 10 days in RPMI1640 medium containing 10% fetal bovine serum) by the conventional method, and this RNA was used as a template for a RT-PCR method (PCR primer1: SEQ ID NO:2, PCR primer 2:SEQ ID NO: 3), to synthesize a gene part containing a region encoding a full length protein of 15K granulysin [Jongstra et al., J. Exp. Med, 165, 601: part corresponding to amino acid sequence of SEQ ID NO:1] as the amplification product of a complementary DNA (cDNA). This cDNA encoding a full length protein of 15K granulysin was incorporated into pRc/CMV or pcDL-SRα296 which is a mammal expression vector, the resulting recombinant vector was dissolved in a physiological saline, and a mouse was immunized with the solution subcutaneously or intracutaneously. After 4 to 5 times immunization at an interval of 1 to 2 weeks, spleen cells obtained from mouse for which increase in an antibody titer was observed by an indirect fluorescent antibody method (performed according to the method described later) was cell-fused according to the conventional method. Then, a hybridoma producing an antibody which specifically binds to granulysin was searched again with an indirect fluorescent antibody method. That is, the cells were transfected with the aforementioned gene encoding 15K granulysin, the expressed cells (Cos7) was fixed with 4% paraformaldehyde, membranes were solubilized with 0.5% Tween 20, the culture supernatant of hybridoma cells was added thereto to react with an antibody, subsequently this was reacted with a fluorescently labeled anti-mouse IgG antibody to detect fluorescence, and whereby, a hybridoma producing an antibody which specifically binds to granulysin was screen. As a result, 9 hybridomas producing antibodies which specifically bind to granulysin were obtained. Using the culture supernatant of each of the resulting hybridomas, ammonium sulfate precipitation and purification by Protein G column were performed to prepare two kinds of monoclonal antibodies to 15K granulysin. Hereinafter, these are referred to monoclonal antibody RF10 (which binds to 15K granulysin, but does not bind to 9K granulysin) and monoclonal antibody RC8 (which binds to both 15K granulysin and 9K granulysin).

(2) Preparation of Polyclonal Antibody to 15K Granulysin

A rabbit was immunized with a conjugate of a partial amino acid sequence (29 amino acids) of granulysin (J. Exp. Med. 165:601-614 (1987), J. Exp. Med., 172:1159-1163 (1990)): Arg Thr Gly Arg Ser Arg Trp Arg Asp Val Cys Arg Asn Phe Met Arg Arg Tyr Gln Ser Arg Val Thr Gln Gly Leu Val Ala Gly (N5-1: SEQ ID NO: 4) and limpet hemocyanin according to the conventional method, to obtain anti-serum. The resulting antiserum was purified by ammonium sulfate precipitation and Protein G column, and further purified by affinity chromatography using a column bound with the aforementioned synthetic peptide (N5-1), to prepare a polyclonal antibody (anti-N5-1 antibody) to granulysin.

(3) Preparation of Granulysin-Containing Culture Supernatant

A gene recombinant vector was produced by incorporating a nucleotide chain of a nucleotide sequence encoding a part corresponding to 15K granulysin protein, among a nucleotide sequence of SEQ ID NO: 1, into pFLAG-CMV vector (manufactured by Sigma) according to the conventional method. As a control, pFLAG-CMV vector in which gene recombination was not performed, was used. Each of these gene recombinant vectors was transfected into a Cos7 cell, and this was cultured at 37° C. under 5% $CO_2$ for 72 hours in DMEM medium (manufactured by Gibco). After completion of the culture, the culture was centrifuged (2500 rpm, 20 min, 4° C.) to obtain the culture supernatant.

Regarding each of the culture supernatants, the proteins were separated by SDS-PAGE. After the protein was transferred from a gel of electrophoresed SDS-PAGE to a nylon membrane, the membrane was blocked with blocking solution (1% skim milk/washing solution). Monoclonal antibody RF10 specific for 15K granulysin was bound to the blocked membrane, and enzyme-labeled anti-mouse antibody and color developing substrate were acted on these, to generate the colored band. As a result, in the supernatant obtained by expressing a gene encoding 15K granulysin protein, a band exhibiting a molecular weight of 15K appeared. However, in the control, this band was not observed. In addition, when the similar test was performed using a polyclonal antibody N5-1 binding to 15K and 9K granulysins, a band showing 15K was observed, but a band showing 9K was not observed.

From this result, it was revealed that 15K granulysin was specifically present in the aforementioned granulysin culture supernatant, but granulysin was not present in the control culture supernatant.

(4) Study of Antibacterial Effect

Lymphocyte separated from human blood was suspended in a culture (RPMI1640, 10% human serum) to be $2 \times 10^7$ cells per 1 ml medium in a plastic culture plate (24 wells/plate) according to the conventional method. Each 1 ml of the medium was dispensed into each well, allowed to leave at 37° C. for 24 hours. Lymphocyte was adhered to a plate surface wall and, in this adherent macrophage, antibacterial effect of 15K granulysin was studied.

Then, 1 ml of RPMI1640 (10% human serum) was added to a well, *M. tuberculosis* (H37Rv, $1 \times 10^5$ to $1 \times 10^6$ cfu) was static-cultured at 37° C. for 4 to 12 hours under 5% $CO_2$, to infect macrophages with *M. tuberculosis*. After the completion of the infection, each 1 ml of supernatant containing 15K granulysin (Grn supernatant) and supernatant in the absence of 15K granulysin (Cont supernatant) was added to a well, this was static-cultured for 2 to 12 hours under the same conditions.

After completing the culture, the culturing supernatant was removed, the adhered cells in a plate were washed with PBS three times, *M. tuberculosis* in the cell was extracted with total 5 ml of 1% aqueous saponin solution. This extract was diluted, seeded on a plate agar medium [7H11 medium (manufactured by Gibco)] and static-cultured at 37° C. for 14 days, and then the number of colonies of *M. tuberculosis* was counted.

The results are shown in FIG. 1.

In FIG. 1, Cont denotes a control culturing supernatant, and Grn denotes a granulysin culture supernatant. A coordinate axis denotes the number of colonies. 1 on an abscissa axis denotes the results obtained by contacting macrophages, *M. tuberculosis* and the culture supernatant, as described above.

2 denotes the result obtained by static-culturing each culture supernatant and *M. tuberculosis* in the absence of macrophages as the same way as 1, washing this, static-culturing this in a 7H11 plate agar medium, and influence of *M. tuberculosis* on non-specific adsorption in a plate was confirmed. 3 denotes the result obtained by static-culturing each 1 ml of the culture supernatant and *M. tuberculosis* at 37° C. for 2 hours in the aforementioned culture plate, and static-culturing this in a 7H11 plate agar medium.

As a result, it was revealed that 15K granulysin has antibacterial effect on *M. tuberculosis* by intervention of macrophages. When there is no intervention of macrophages, antibacterial effect of 15K granulysin on *M. tuberculosis* was not perceived.

By the aforementioned Test Example, antibacterial activity was shown in 15K granulysin, and it was revealed that 15K granulysin can be used as an active ingredient of a therapeutic agent for infections. It has been reported that, when 15K granulysin was transfected into cells such as Cos7 cells, HeLa and PC12, 15K granulysin was detected in the culture supernatant, but there was no damage in the cells. When 9K granulysin was used in place of 15K granulysin in the presence of perforin, cytotoxic activity or apoptosis is induced (Pena, S. V. et al, J. Immunol., 158, 2680-2688(1997)).

(Synergetic Effect)

Next, improvements of killing effect on bacteria by using (1) 15K granulysin recombinant protein and 15K granulysin in vivo expression vector, (2) 15K granulysin recombinant protein and at least one interleukin selected from IL-6, IL-23 or IL-27, (3) 15K granulysin in vivo expression vector and at least one interleukin selected from IL-6, IL-23 or IL-27, and (4) 15K granulysin in vivo expression vector and HSP65DNA and IL-12 DNA in vivo expression vectors.

"Synergetic effect" used herein means effect when a combined use of more than two materials improves killing effect on bacteria compared to an independent use of the materials.

G1 to G10 groups used in the examples are shown in FIG. 1.

| <FIG. 1> |
|---|
| G1 Control |
| G2 15K granulysin recombinant protein and 15K granuysin in vivo expression vector were administered on the same day. |
| G3 15K granulysin recombinant protein and Interleukin (IL-6 or IL-23) were administered alternately. |
| G4 15K granulysin in vivo expression vector and interleukin (IL-23 or IL-27) were administered alternately. |
| G5 Only 15K granulysin recombinant protein was administered in the same day as the administration of 15K granulysin recombinant protein in G2 or G3. |
| G6 Only 15K granulysin in vivo expression vector was administered in the same day as the administration of 15K granulysin in vivo expression vector in G2, G4 or G11. |
| G7 Only interleukin (IL-6, IL-23 or IL-27) was administered in the same day as the administration of Interleukin in G3 or G4. |
| G9 15K granulysin in vivo expression vector was administered in the first half of the experimental period, and interleukin (IL-6) was administered in the last half of the experimental period. |
| G10 Only interleukin (IL-6) was administered in the same day as the administration of interleukin in G9. |
| G11 15K granulysin in vivo expression vector and HSP65DNA and IL-12 DNA in vivo expression vectors were administered alternately. |
| G12 Only HSP65DNA and IL-12 DNA in vivo expression vectors were administered in the same day as the |

| -continued |
|---|
| <FIG. 1> |
| administration of HSP65DNA and IL-12 DNA in vivo expression vectors in G11. |

(Reagent)

15K granulysin recombinant protein was obtained from R&D System Co (Minneapolis, Minn.). IL-6 was obtained from Miltenyi Biotec Co. (Auburn, Calif.). Recombinant mouse IL-23 and recombinant mouse IL-27 were obtained from R&D System Co.

15K granulysin in vivo expression vector was prepared by inserting 15K granulysin gene into CAG vector, and incorporating the obtained vector into an envelope of Sendai virus (HVJ: Hemagglutinating Virus of Japan). HSP65DNA and IL-12 DNA in vivo expression vectors were prepared by inserting their genes respectively into pcDNA3.1 vectors, and incorporating the obtained vectors into an envelope of Sendai virus (HVJ: Hemagglutinating Virus of Japan). DBA/1 and BALB/c mice were used. These mice are easily infected by *M. tuberculosis*. For statistical analysis, Student's t Test was used.

In the following examples, in the case of an administration of 15K granulysin recombinant protein, 4 μg was administered per 1 mouse (20 g) per day. In the case of an administration of granulysin in vivo expression vector, 100 μg/0.2 ml was intramuscularly administered per 1 mouse (20 g) per day by 50 μg in an anterior tibial muscle in both sides of inferior limbs. In the case of an administration of IL-6, 1 μg per 1 mouse (20 g) per day ($>=5 \times 10^4$ International Unit), in the case of an administration of IL-23, 2 μg per 1 mouse (20 g) per day ($>=5 \times 10^4$ International Unit), and in the case of an administration of IL-27, 1 μg per 1 mouse (20 g) per day ($>=5 \times 10^4$ International Unit) were intraperitoneally administered by dividing the amounts to three (by ⅓).

*M. tuberculosis* to be used for the infection was *M. tuberculosis* H37Rv (human type). In the case of an intraperitoneal infection of *M. tuberculosis*, $1 \times 10^7$ CFU was suspended with 0.2 ml of saline, and this was administered intraperitoneally. In the case of a lung infection (intratracheal infection) of *M. tuberculosis*, $1 \times 10^3$ CFU was administered into a respiratory passage of the mouse in an aerosol chamber.

Experiment 1

Synergetic Effect of 15K Granulysin Recombinant Protein and 15K Granulysin In Vivo Expression Vector on *M. Tuberculosis* when Infected Intraperitoneally 8 weeks old DBA/1 mice was intraperitoneally infected with *M. tuberculosis*. The mice were divided into a group with no administration (G1), a group with administrations of 15K granulysin recombinant protein and 15K granulysin in vivo expression vector (G2), a group with an administration of only 15K granulysin recombinant protein (G5), and a group with an administration of only 15K granulysin in vivo expression vector (G6).

In G2, 15K granulysin recombinant protein was administered 4 times at intervals, and 15K granulysin in vivo expression vector was administered 7 times at intervals. In G5, only 15K granulysin recombinant protein, and in G6, only 15K granulysin in vivo expression vector, were administered respectively on the same day as G2. Nothing was administered in G1.

Then, these mice were dissected after euthanasia to obtain liver tissues including liver cells. The obtained tissues were homogenized and cultured on a 7H11 plate agar medium for 14 days. The number of colonies of *M. tuberculosis* was counted.

As a result, the number of colonies in G2 was fewer than those in G5 and G6. The numbers of colonies of 3 mice from each group were put in $\log_{10}$ in order to perform a statistical analysis, and the number of *M. tuberculosis* in G2 was more reduced than those in G5 and G6 with a statistically significant difference ($p<0.05$).

Figure 2:
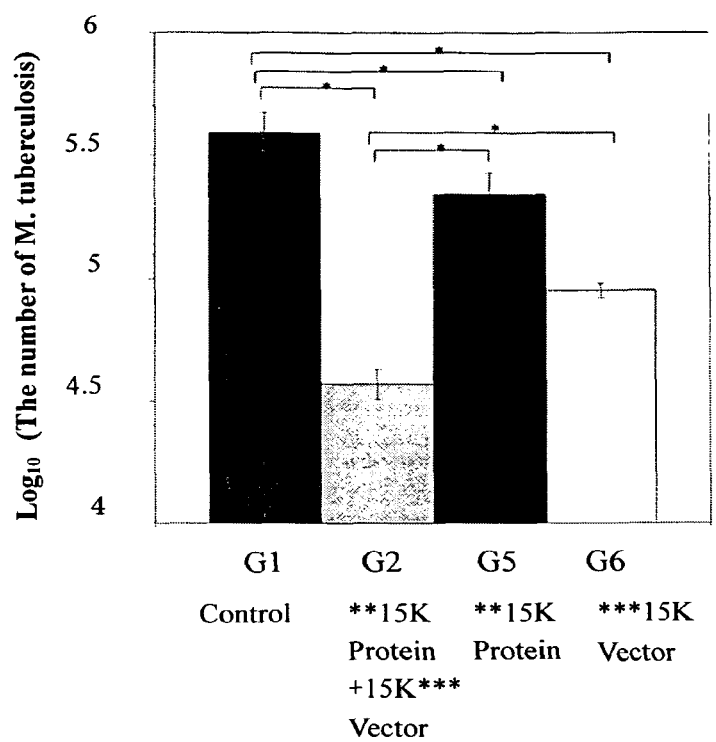
FIG. 2 is a view showing treatment effects of 15K granulysin recombinant protein and 15K granulysin in vivo expression vector in liver of mice (DBA/1) intraperitoneally-infected with *M. tuberculosis*.

In addition, the statistical analysis was performed in G1, which is a control, and G2, G5 and G6 in the same way, and the numbers of *M. tuberculosis* in G2, G5 and G6 were more reduced than that in G1 with a statistically significant difference ($p<0.05$) (See FIG. 2).

Accordingly, 15K granulysin recombinant protein and 15K granulysin in vivo expression vector independently exhibit effects in a liver, however, the combination of the above enables to significantly improve the killing effect on *M. tuberculosis* and show the synergetic effect.

Experiment 2

Synergetic Effect of 15K Granulysin Recombinant Protein and IL-6 on *M. tuberculosis* in DBA/1 Mouse 8 weeks old DBA/1 mice was lung-infected with *M. tuberculosis* in an aerosol chamber. The mice were divided into a group with no administration (G1), a group with administrations of 15K granulysin recombinant protein and IL-6 (G3), a group with an administration of only 15K granulysin recombinant protein (G5), and a group with an administration of only IL-6 (G7).

In G3, 15K granulysin recombinant protein and IL-6 were alternately administered 6 times each. In G5, only 15K granulysin recombinant protein, and in G7, only IL-6, were administered 6 times respectively. Nothing was administered in G1.

Then, these mice were dissected after euthanasia to obtain spleen tissues including spleen cells. The obtained tissues were homogenized and cultured on a 7H11 plate agar medium for 14 days. The number of colonies of *M. tuberculosis* was counted.

As a result, the number of colonies in G3 was fewer than those in G5 and G7. The numbers of colonies of 3 mice from each group were put in $\log_{10}$ in order to perform the statistical analysis, and the number of *M. tuberculosis* in G3 was more reduced than those in G5 and G7 with a statistically significant difference ($p<0.05$).

Figure 3:
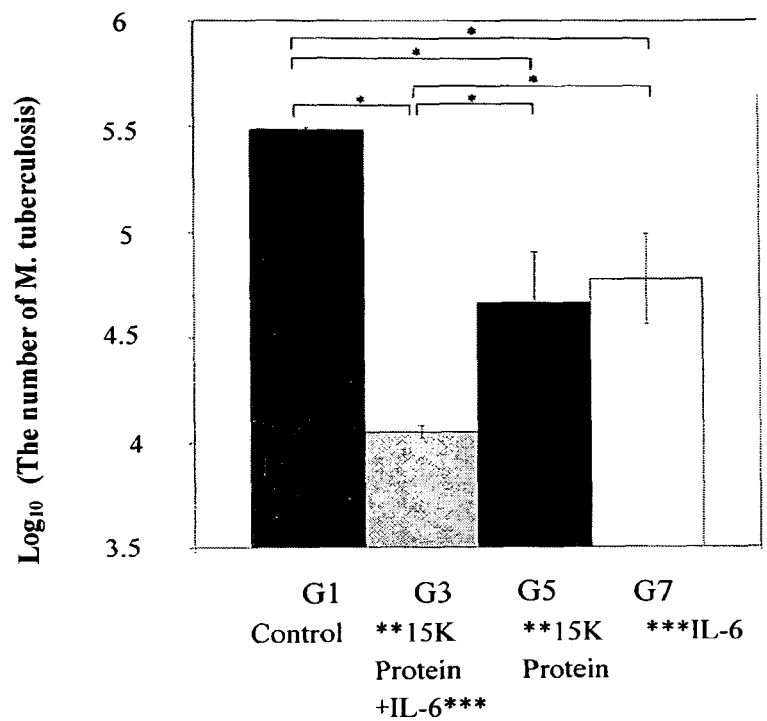
FIG. 3 is a view showing treatment effects of 15K granulysin recombinant protein and IL-6 in spleen of mice (DBA/1) infected with *M. tuberculosis* by aerosol.

In addition, the statistical analysis was performed in G1, which is a control, and G3, G5 and G7 in the same way, and the numbers of *M. tuberculosis* in G3, G5 and G7 were more reduced than that in G1 with a statistically significant difference ($p<0.05$) (See FIG. 3).

Accordingly, 15K granulysin recombinant protein and Il-6 independently show the effect in a spleen, however, the combination of the above enables to significantly improve the killing effect on *M. tuberculosis*, and show the synergetic effect.

Experiment3

Synergetic Effect of 15K Granulysin In Vivo Expression Vector and IL-6 on *M. tuberculosis*

8 weeks old DBA/1 mice was lung-infected with *M. tuberculosis* in an aerosol chamber. The mice were divided into a group with no administration (G1), a group with administrations of 15K granulysin in vivo expression vector and IL-6 (G9), a group with an administration of only 15K granulysin in vivo expression vector (G6), and a group with an administration of only IL-6 (G10).

In G9, 15K granulysin in vivo expression vector and IL-6 were administered 6 times respectively. 15K granulysin in vivo expression vector was administered in the first half of the experimental period, and IL-6 was administered in the last half of the experimental period. In G6, only 15K granulysin in vivo expression vector, and in G10, only IL-6, were administered 6 times respectively. Nothing was administered in G1.

Then, these mice were dissected after euthanasia to obtain spleen tissues including spleen cells. The obtained tissues were homogenized and cultured on a 7H11 plate agar medium for 14 days. The number of colonies of *M. tuberculosis* was counted.

As a result, the number of colonies in G9 was fewer than those in G6 and G10. The numbers of colonies of 3 mice from each group were put in $\log_{10}$ in order to perform the statistical analysis, and the number of *M. tuberculosis* of G9 was more reduced than those of G6 and G10 with a statistically significant difference ($p<0.05$).

Figure 4:
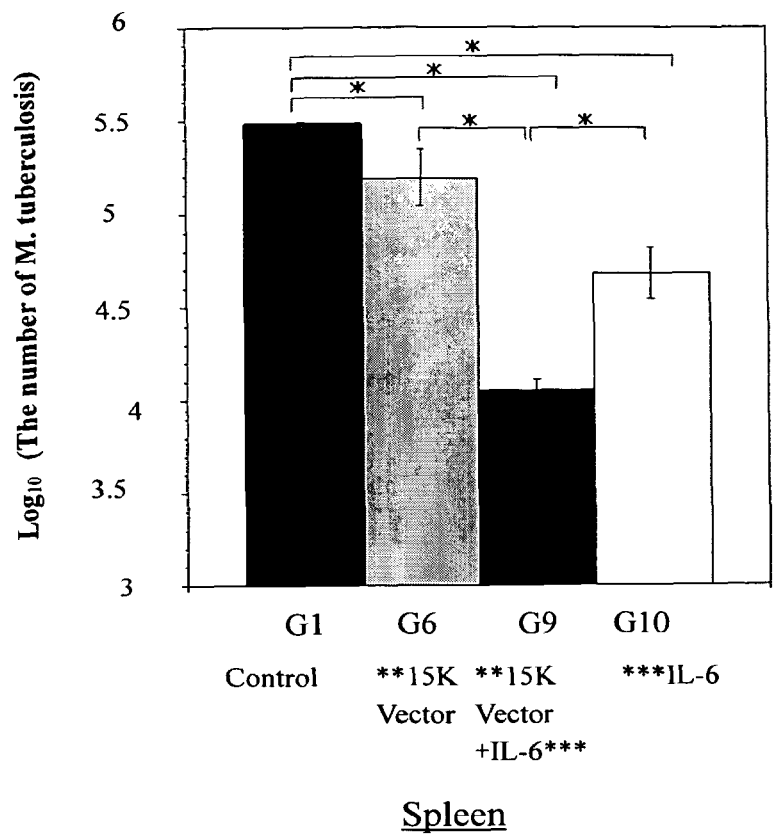
FIG. 4 is a view showing treatment effects of 15K granulysin in vivo expression vector and IL-6 in spleen of mice (DBA/1) infected with *M. tuberculosis* by aerosol.

In addition, the statistical analysis was performed in G1, which is a control, and G9, G6 and G10 in the same way, and the numbers of *M. tuberculosis* in G9, G6 and G10 were more reduced than that in G1 with a statistically significant difference ($p<0.05$) (See FIG. 4).

Accordingly, the combined use of 15K granulysin in vivo expression vector and IL-6 significantly improves the killing effect on *M. tuberculosis* in a spleen compared to the independent use of the above materials, and show the synergetic effect.

Experiment 4

Synergetic Effect of 15K Granulysin Recombinant Protein and IL-6 on *M. tuberculosis* in BALB/c Mouse BALB/c mice, which are commonly used in experiments of *tuberculosis* infection, were lung-infected with *M. tuberculosis* in an aerosol chamber. The mice were divided into a group with no administration (G1), a group with administrations of 15K granulysin recombinant protein and IL-6 (G3), a group with an administration of only 15K granulysin recombinant protein (G5), and a group with an administration of only IL-6 (G7).

In G3, 15K granulysin recombinant protein and IL-6 were alternately administered 6 times each. In G5, only 15K granulysin recombinant protein, and in G7, only IL-6, were administered 6 times respectively. Nothing was administered in G1.

Then, these mice were dissected after euthanasia to obtain liver tissues including liver cells and lung tissues including lung cells. The obtained tissues were homogenized and cultured on a 7H11 plate agar medium for 14 days. The number of colonies of *M. tuberculosis* was counted.

As a result, the number of colonies in G3 was fewer than those in G5 and G7. The numbers of colonies of 3 mice from each group were put in $\log_{10}$ in order to perform the statistical analysis, and the number of *M. tuberculosis* of G3 was more reduced than those of G5 and G7 with a statistically significant difference ($p<0.05$).

Figure 5:
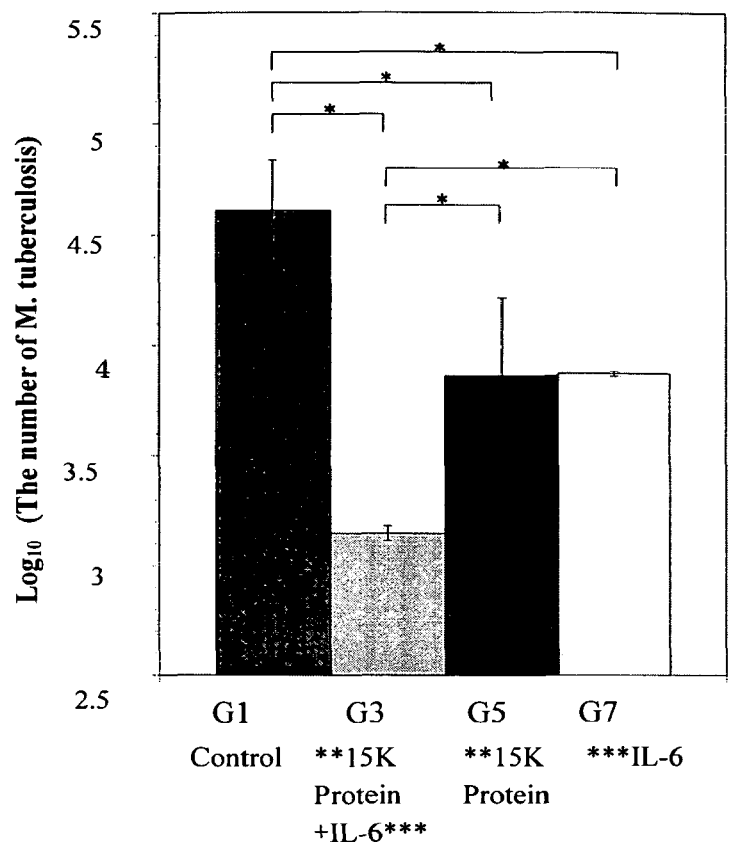
FIG. 5 is a view showing treatment effects of 15K granulysin recombinant protein and IL-6 in liver of mice (BALB/c) infected with *M. tuberculosis* by aerosol.
Figure 6:
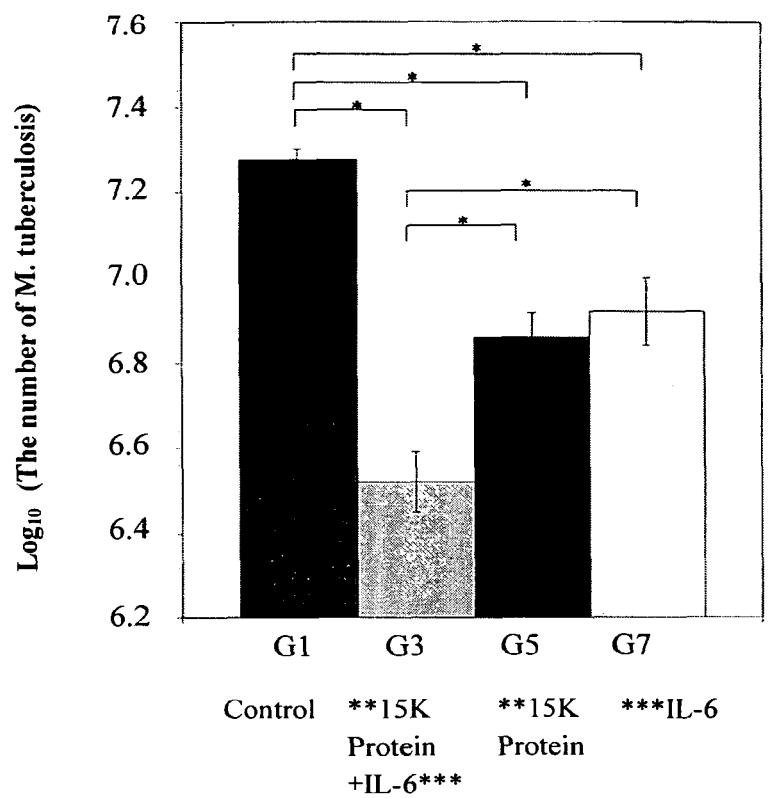
FIG. 6 is a view showing treatment effects of 15K granulysin recombinant protein and IL-6 in lung of mice (BALB/c) infected with *M. tuberculosis* by aerosol.

In addition, the statistical analysis was performed in G1, which is a control, and G3, G5 and G7 in the same way, and the numbers of *M. tuberculosis* in G3, G5 and G7 were more reduced than that in G1 with a statistically significant difference (p<0.05) (See FIG. 5 (Liver) and FIG. 6 (Lung)).

Accordingly, 15K granulysin and IL-6 exhibit effects in liver and lung independently, however, the combination of the above enables to significantly improve the killing effect on *M. tuberculosis* and show the synergetic effect.

Experiment 5

Synergetic Effect of 15K Granulysin Recombinant Protein and 15K Granulysin In Vivo Expression Vector on *M. Tuberculosis* in DBA/1 Mouse when Lung-Infected 8 weeks old DBA/1 mice were lung-infected with *M. tuberculosis* in an aerosol chamber. The mice were divided into a group with administrations of 15K granulysin recombinant protein and 15K granulysin in vivo expression vector (G2), a group with an administration of only 15K granulysin recombinant protein (G5), and a group with an administration of only 15K granulysin in vivo expressing vector (G6).

In G2, 15K granulysin recombinant protein and 15K granulysin in vivo expression vector were administered 6 times at intervals in the same day. In G5, only 15K granulysin recombinant protein, and in G7, only 15K granulysin in vivo expression vector, were administered 6 times respectively.

Then, these mice were dissected after euthanasia to obtain liver tissues including liver cells. The obtained tissues were homogenized and cultured on a 7H11 plate agar medium for 14 days. The number of colonies of *M. tuberculosis* was counted.

Figure 7:
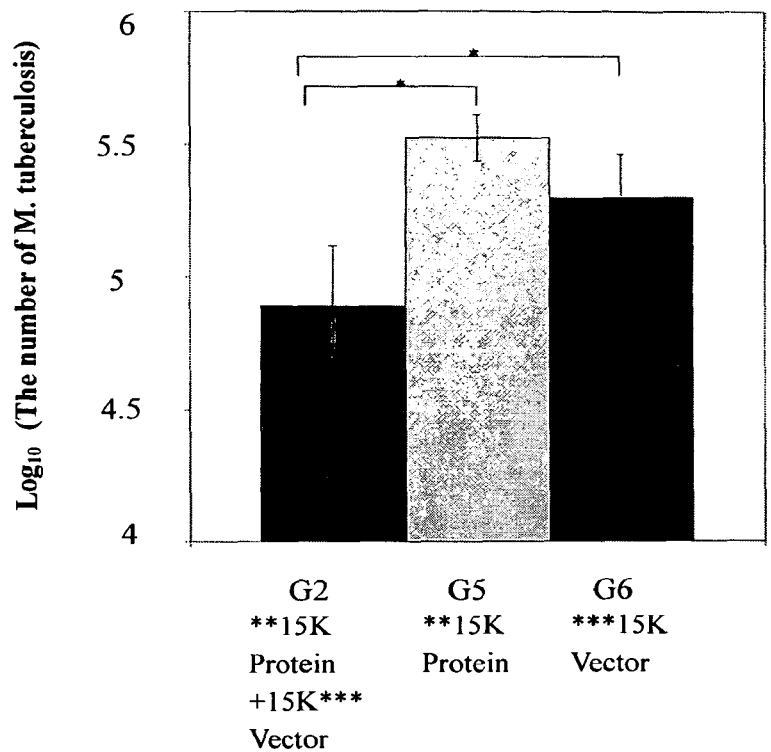
FIG. 7 is a view showing treatment effects of 15K granulysin recombinant protein and 15K granulysin in vivo expression vector in liver of mice (DBA/1) infected with *M. tuberculosis* by aerosol.

As a result, the number of colonies in G2 was fewer than those in G5 and G6. The numbers of colonies of 3 mice from each group were put in $\log_{10}$ in order to perform the statistical analysis, and the number of *M. tuberculosis* in G2 was more reduced than those in G5 and G6 with a statistically significant difference (p<0.05) (See FIG. 7).

Accordingly, the combination of 15K granulysin recombinant protein and 15K granulysin in vivo expression vector in liver significantly improve the killing effect on *M. tuberculosis* and show the synergetic effect.

Experiment 6

Synergetic Effect of 15K Granulysin Recombinant Protein and 15K Granulysin In Vivo Expression Vector on *M. tuberculosis* When Lung-Infected 8 weeks old DBA/1 mice were lung-infected with *M. tuberculosis* in an aerosol chamber. The mice were divided into a group with no administration (G1), a group with administrations of 15K granulysin recombinant protein and 15K granulysin in vivo expression vector (G2), a group with an administration of only 15K granulysin recombinant protein (G5), and a group with an administration of 15K granulysin in vivo expression vector (G6).

In G2, 15K granulysin recombinant protein and 15K granulysin in vivo expression vector were alternately administered 6 times each in the same day. In G5, only 15K granulysin recombinant protein, and in G6, only 15K granulysin in vivo expression vector, were administered 6 times respectively. Nothing was administered in G1.

Then, these mice were dissected after euthanasia to obtain spleen tissues including spleen cells. The obtained tissues were homogenized and cultured on a 7H11 plate agar medium for 14 days. The number of colonies of *M. tuberculosis* was counted.

As a result, the number of colonies in G2 was fewer than those in G5 and G6. The numbers of colonies of 3 mice from each group were put in $\log_{10}$ in order to perform the statistical analysis, and the number of *M. tuberculosis* in G2 was more reduced than those in G5 and G6 with a statistically significant difference (p<0.05).

Figure 8:
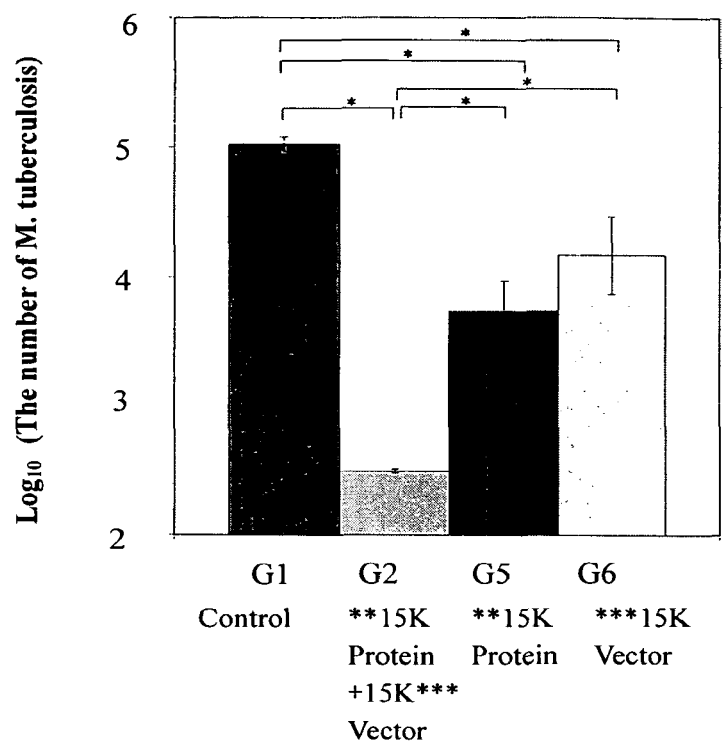
FIG. 8 is a view showing treatment effects of 15K granulysin recombinant protein and 15K granulysin in vivo expression vector in spleen of mice (DBA/1) infected with *M. tuberculosis* by aerosol.

In addition, the statistical analysis was performed in G1, which is a control, and G2, G5 and G6 in the same way, and the number of *M. tuberculosis* in G2 was more reduced than those in G5 and G6 with a statistically significant difference (p<0.05) (See FIG. 8).

Accordingly, 15K granulysin recombinant protein and 15K granulysin in vivo expression vector exhibit effects in spleen independently, however, the combination of the above enables to significantly improve the killing effect on *M. tuberculosis* and show the synergetic effect.

Experiment 7

Synergetic Effect of 15K Granulysin Recombinant Protein and IL-23 on *M. tuberculosis*

DBA/1 mice were lung-infected with *M. tuberculosis* in an aerosol chamber. The mice were divided into a group with no administration (G1), a group with administrations of 15K granulysin recombinant protein and IL-23 (G3), a group with an administration of only 15K granulysin recombinant protein (G5), and a group with an administration of only IL-23 (G7).

In G3, 15K granulysin recombinant protein and IL-23 were alternately administered 6 times each. In G5, only 15K granulysin, and in G7, only IL-23, were administered 6 times respectively. Nothing was administered in G1.

Then, these mice were dissected after euthanasia to obtain spleen, liver and lung tissues including spleen, liver and lung cells respectively. The obtained tissues were homogenized and cultured on a 7H11 plate agar medium for 14 days. The number of colonies of *M. tuberculosis* was counted.

As a result, in all of spleen, liver and lung organs, the number of colonies in G3 was fewer than those in G5 and G7. The numbers of colonies of 3 mice from each group were put in $\log_{10}$ in order to perform the statistical analysis, and the number of *M. tuberculosis* in G3 was more reduced than those in G5 and G7 with a statistically significant difference (p<0.05).

Figure 9:
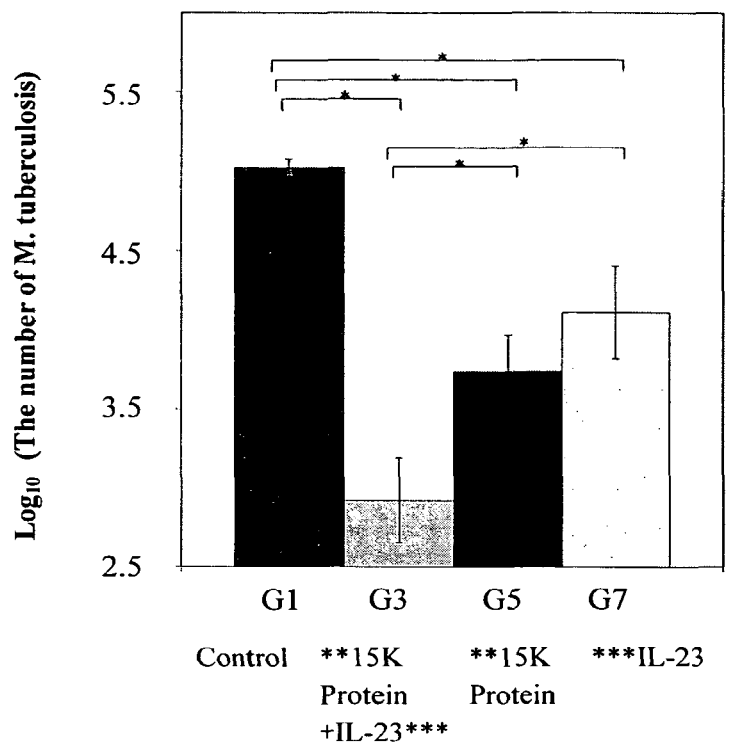
FIG. 9 is a view showing treatment effects of 15K granulysin recombinant protein and IL-23 in spleen of mice (DBA/1) infected with *M. tuberculosis* by aerosol.
Figure 10:
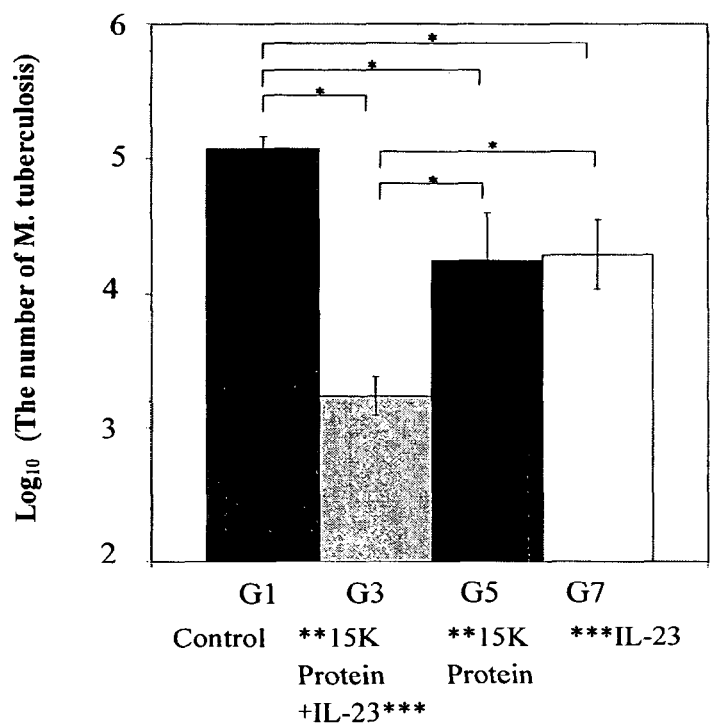
FIG. 10 is a view showing treatment effects of 15K granulysin recombinant protein and IL-23 in liver of mice (DBA/1) infected with *M. tuberculosis* by aerosol.
Figure 11:
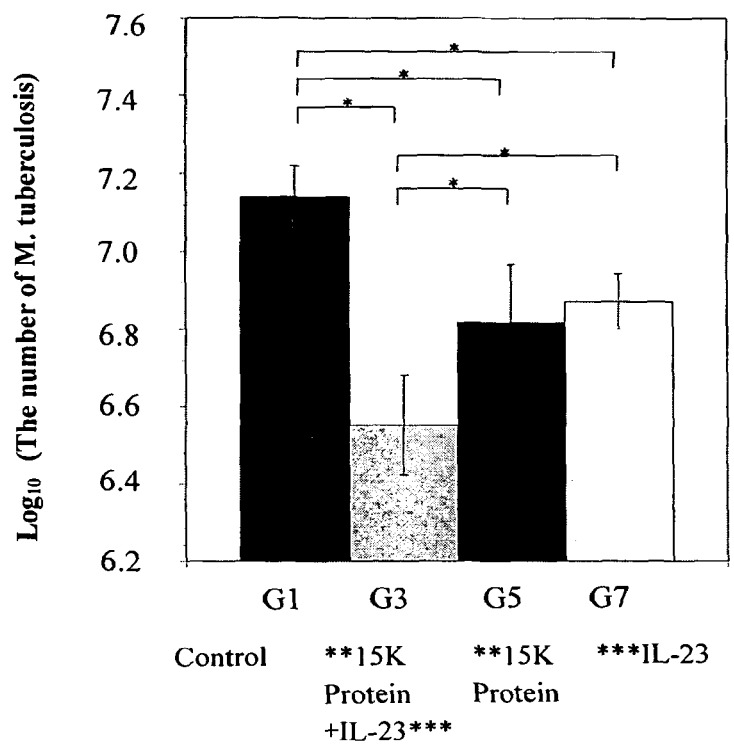
FIG. 11 is a view showing treatment effects of 15K granulysin recombinant protein and IL-23 in lung of mice (DBA/1) infected with *M. tuberculosis* by aerosol.

In addition, the statistical analysis was performed in G1, which is a control, and G3, G5 and G7 in the same way, and the numbers of *M. tuberculosis* in G3, G5 and G7 were more reduced than that in G1 with a statistically significant difference (p<0.05) (See FIG. 9 (spleen), FIG. 10 (liver), and FIG. 11 (lung)).

Accordingly, 15K granulysin and IL-23 independently exhibit effects in all of spleen, liver and lung, however, the combination of the above enables to significantly improve the killing effect on *M. tuberculosis* and show the synergetic effect.

Experiment 8

Synergetic Effect of 15K Granulysin In Vivo Expression Vector and IL-23 on *M. tuberculosis*

DBA/1 mice were lung-infected with *M. tuberculosis* in an aerosol chamber. The mice were divided into a group with no administration (G1), a group with administrations of 15K granulysin in vivo expression vector and IL-23 (G4), a group with an administration of only 15K granulysin in vivo expression vector (G6), and a group with an administration of only IL-23 (G7).

In G4, 15K granulysin in vivo expression vector and IL-23 were alternately administered 6 times each. In G6, only 15K granulysin in vivo expression vector, and in G7, only IL-23, were administered 6 times respectively. Nothing was administered in G1.

Then, these mice were dissected after euthanasia to obtain spleen tissues including spleen cells. The obtained tissues were homogenized and cultured on a 7H11 plate agar medium for 14 days. The number of colonies of M. tuberculosis was counted.

As a result, the number of colonies in G4 was fewer than those in G6 and G7. The numbers of colonies of 3 mice from each group were put in $\log_{10}$ in order to perform the statistical analysis, and the number of M. tuberculosis in G4 was more reduced than those in G6 and G7 with a statistically significant difference ($p<0.05$).

Figure 12:
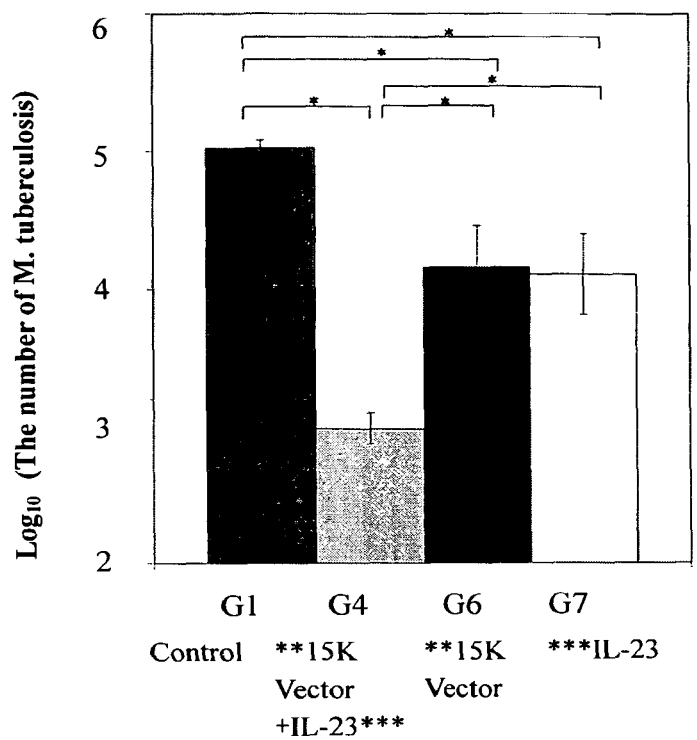
FIG. 12 is a view showing treatment effects of 15K granulysin in vivo expression vector and IL-23 in spleen of mice (DBA/1) infected with *M. tuberculosis* by aerosol.

In addition, the statistical analysis was performed in G1, which is a control, and G4, G6 and G7 in the same way, and the numbers of M. tuberculosis in G4, G6 and G7 were more reduced than that in G1 with a statistically significant difference ($p<0.05$) (See FIG. 12).

Accordingly, 15K granulysin in vivo expression vector and IL-23 exhibit effects in spleen independently, however, the combination of the above enables to significantly improve the killing effect on M. tuberculosis and show the synergetic effect.

Experiment 9

Synergetic Effect of 15K Granulysin In Vivo Expression Vector and IL-27 on M. tuberculosis BALB/c mice were lung-infected with M. tuberculosis in an aerosol chamber. The mice were divided into a group with administrations of 15K granulysin in vivo expression vector and IL-27 (G4), a group with an administration of only 15K granulysin in vivo expression vector (G6), and a group with an administration of only IL-27 (G7).

In G4, 15K granulysin in vivo expression vector and IL-27 were alternately administered 6 times each. In G6, only 15K granulysin in vivo expression vector, and in G7, only IL-27, were administered 6 times respectively.

Then, these mice were dissected after euthanasia to obtain lung tissues including lung cells. The obtained tissues were homogenized and cultured on a 7H11 plate agar medium for 14 days. The number of colonies of M. tuberculosis was counted.

Figure 13:
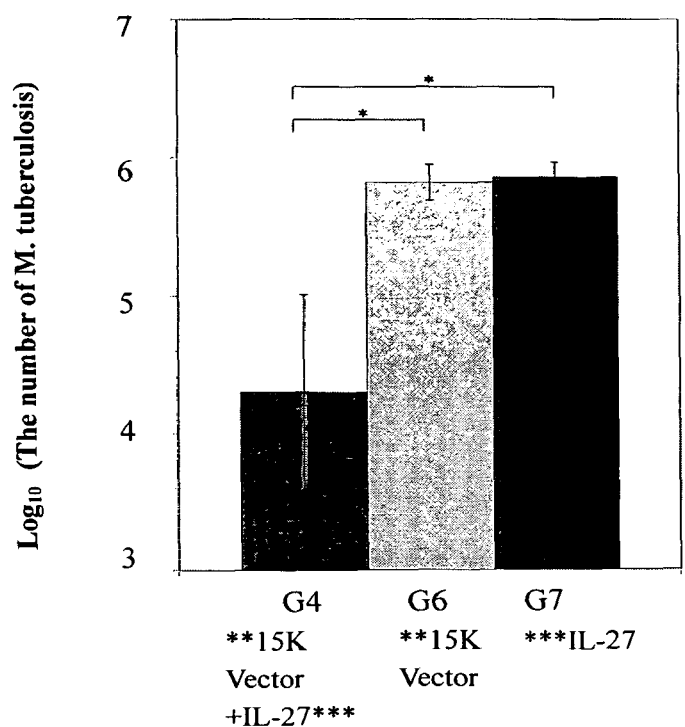
FIG. 13 is a view showing treatment effects of 15K granulysin recombinant protein and IL-27 in lung of mice (BALB/c) infected with *M. tuberculosis* by aerosol.

As a result, the number of colonies in G4 was fewer than those in G6 and G7. The numbers of colonies of 3 mice from each group were put in $\log_{10}$ in order to perform the statistical analysis, and the number of M. tuberculosis in G4 was more reduced than those in G6 and G7 with a statistically significant difference ($p<0.05$) (See FIG. 13).

Accordingly, the combination of 15K granulysin in vivo expression vector and IL-27 in lung significantly improves the killing effect on M. tuberculosis and shows the synergetic effect.

Experiment 10

Synergetic Effect of 15K Granulysin In Vivo Expression Vector and HSP65DNA and IL-12DNA In Vivo Expression Vectors on M. tuberculosis 8 weeks old DBA/1 mice were lung-infected with M. tuberculosis in an aerosol chamber. The mice were divided into a group with administrations of 15K granulysin in vivo expression vector and HSP65DNA and IL-12DNA in vivo expression vectors (G11), a group with an administration of only 15K granulysin in vivo expression vector (G6), and a group with an administration of only HSP65DNA and IL-12DNA in vivo expression vectors (G12).

In G11, 15K granulysin in vivo expression vector and HSP65DNA and IL-12DNA in vivo expression vectors were alternately administered 6 times each. In G6, only 15K granulysin in vivo expression vector, and in G12, only HSP65DNA and IL-12DNA in vivo expression vectors, were administered 6 times respectively.

Then, these mice were dissected after euthanasia to obtain liver tissues including liver cells. The obtained tissues were homogenized and cultured on a 7H11 plate agar medium for 14 days. The number of colonies of M. tuberculosis was counted.

Figure 14:
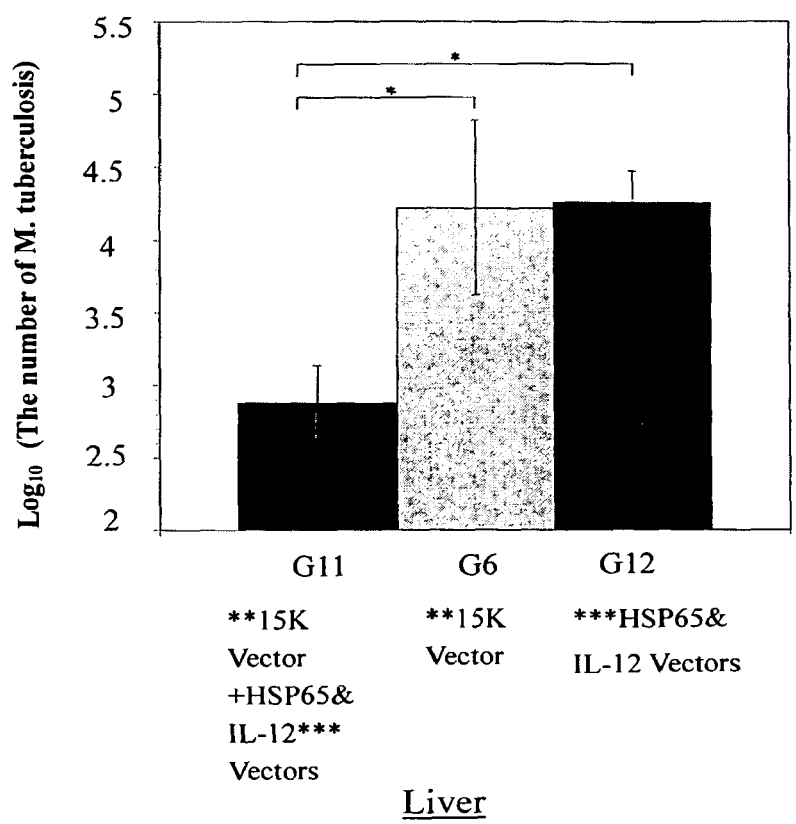
FIG. 14 is a view showing treatment effects of 15K granulysin in vivo expression vector and HSP65DNA and IL-12DNA in vivo expression vectors in liver of mice (DBA/1) infected with *M. tuberculosis* by aerosol.

As a result, the number of colonies in G11 was fewer than those in G6 and G12. The numbers of colonies of 3 mice from each group were put in $\log_{10}$ in order to perform the statistical analysis, and the number of M. tuberculosis in G11 was more reduced than those in G6 and G12 with a statistically significant difference ($p<0.05$) (See FIG. 14).

Accordingly, the combined use of 15K granulysin in vivo expression vector and HSP65DNA and IL-12DNA in vivo expression vectors in liver significantly improves the killing effect on M. tuberculosis compared to the independent use of the above materials, and shows the synergetic effect.

What is claimed is:

1. A treatment method comprising a step for administrating a therapeutic agent for *tuberculosis* into a living body, wherein
the therapeutic agent comprises as active ingredients:
a vector in which a gene encoding 15K granulysin is incorporated to express 15K granulysin in vivo; and
at least one interleukin selected from the group consisting of interleukin 6, interleukin 23 and interleukin 27; whereby cytotoxicity is not shown in spite of not using perforin as said therapeutic agent.

* * * * *